United States Patent
Steffens et al.

(10) Patent No.: US 10,239,826 B2
(45) Date of Patent: Mar. 26, 2019

(54) METHOD FOR PRODUCING ISOCYANATES

(71) Applicant: Covestro Deutschland AG, Leverkusen (DE)

(72) Inventors: Friedhelm Steffens, Leverkusen (DE); Bastian Mahr, Bergisch Gladbach (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 15/744,239

(22) PCT Filed: Jul. 12, 2016

(86) PCT No.: PCT/EP2016/066474
§ 371 (c)(1),
(2) Date: Jan. 12, 2018

(87) PCT Pub. No.: WO2017/009311
PCT Pub. Date: Jan. 19, 2017

(65) Prior Publication Data
US 2018/0194720 A1    Jul. 12, 2018

(30) Foreign Application Priority Data
Jul. 16, 2015  (EP) .................... 15176964

(51) Int. Cl.
| | |
|---|---|
| C07C 263/10 | (2006.01) |
| C07C 263/20 | (2006.01) |
| B01D 3/16 | (2006.01) |
| B01D 3/42 | (2006.01) |

(52) U.S. Cl.
CPC .............. *C07C 263/10* (2013.01); *B01D 3/16* (2013.01); *B01D 3/42* (2013.01); *C07C 263/20* (2013.01)

(58) Field of Classification Search
CPC ....... C07C 263/10; C07C 263/20; B01D 3/42; B01D 3/16
See application file for complete search history.

(56) References Cited

U.S. PATENT DOCUMENTS

| | | | |
|---|---|---|---|
| 2,764,607 A | 9/1956 | Hieserman et al. | |
| 3,544,611 A | 12/1970 | Michelet et al. | |
| 5,449,818 A | 9/1995 | Biskup et al. | |
| 5,633,396 A | 5/1997 | Bischof et al. | |
| 6,800,781 B2 | 10/2004 | Herold et al. | |
| 7,112,694 B2* | 9/2006 | Woelfert | C07C 263/10 422/653 |
| 7,118,653 B2 | 10/2006 | Brady et al. | |
| 7,584,629 B2 | 9/2009 | Sohn et al. | |
| 7,645,900 B2 | 1/2010 | Lorenz et al. | |
| 7,915,444 B2 | 3/2011 | Woelfert et al. | |
| 8,288,584 B2 | 10/2012 | Knoesche et al. | |
| 8,563,768 B2* | 10/2013 | Bruns | C07C 263/10 560/347 |
| 8,692,016 B2 | 4/2014 | Sanders et al. | |
| 9,024,057 B2 | 5/2015 | Biskup et al. | |
| 2010/0041915 A1 | 2/2010 | Woelfert et al. | |

FOREIGN PATENT DOCUMENTS

| | | |
|---|---|---|
| DE | 100 27 779 A1 | 12/2001 |
| GB | 737 442 A | 9/1955 |

OTHER PUBLICATIONS

Kister, Henry Z., Distillation Operation, McGraw Hill Professional, Ch. 17.2, 1990 (abstract).
Chemie Ingenieur Technik, vol. 44 (18): 1051-1056, Sep. 1972 (abstract).
Branan, Carl R., Process Evaluation—What Size Should a Plant Be?, Rules of Thumb for Chemical Engineers, 4th ed, p. 240-273, 2005 (abstract).
Weinhem, Chemical Plant Design and Construction, Ullmann's Encyclopedia of Industrial Chemistry, vol. 8: 273, 2012.

* cited by examiner

*Primary Examiner* — Paul A Zucker
(74) *Attorney, Agent, or Firm* — Donald R. Palladino

(57) ABSTRACT

A method for producing isocyanates by reacting primary amines with phosgene in a stoichiometric excess in the gas phase, wherein the excess phosgene is subsequently recovered and recirculated back into the reaction. particular a method for the feedback-controlled recirculation of the recovered phosgene, particularly when the phosgene stream that should be recovered is distributed between multiple gas-phase reactors operated in parallel.

16 Claims, No Drawings

METHOD FOR PRODUCING ISOCYANATES

CROSS-REFERENCE TO RELATED APPLICATIONS

This application is a national stage application under 35 U.S.C. § 371 of PCT/EP2016/066474, filed Jul. 12, 2016, which claims the benefit of European Application No. 15176964.3, filed Jul. 16, 2015, both of which are being incorporated by reference herein.

FIELD

The invention relates to a process for preparing isocyanates by reaction of primary amines with phosgene in a stoichiometric excess in the gas phase, wherein the excess phosgene is subsequently recovered and recirculated to the reaction. The present invention relates in particular to a process for the regulated recirculation of the recovered phosgene, in particular when the phosgene stream to be recirculated is divided over a plurality of gas-phase reactors operated in parallel.

BACKGROUND

Isocyanates are produced in large quantities and serve mainly as starting materials for the preparation of polyurethanes. They are usually prepared by reaction of the corresponding amines with phosgene, with phosgene being used in a stoichiometric excess. The reaction of the amines with the phosgene can be carried out either in the gas phase or in the liquid phase. In these syntheses, the excess phosgene is generally obtained at least partly together with the gaseous by-product hydrogen chloride liberated in the reaction, so that separating off the excess phosgene from the by-product hydrogen chloride and recirculating it to the reaction is indispensable for economical operation of an isocyanate synthesis. Particularly when the phosgene stream to be recirculated is divided over a plurality of reactors, ensuring the intended phosgene flow to each individual reactor, especially under non-steady-state operating conditions, represents a special technical challenge, so that ensuring a sufficient and stable pressure in phosgene production is of considerable importance.

Various processes for preparing isocyanates by reaction of amines with phosgene in the gas phase are known from the prior art.

GB 737 442 describes a process for recovering liquid phosgene from gas mixtures containing hydrogen chloride and phosgene, in which the gas mixture flows upward through a cooler which is cooled to from −40 to −60° C., with the phosgene condensing and running down into a stock tank. This document states that the recovered liquid phosgene can, owing to its low content of hydrogen chloride of less than 0.7% by weight, be used without further purification in reactions with amines. However, it gives no information as to how the recovered liquid phosgene can be used in an economically advantageous way in a gas-phase reaction. In addition, the process disclosed has the disadvantage that the hydrogen chloride gas leaving the cooler still contains appreciable amounts of phosgene which are thus lost to the phosgenation reaction. A further disadvantage is that the condensation is carried out at a very low and thus energy-consuming temperature level.

U.S. Pat. No. 2,764,607 describes a process for recovering phosgene from a gas mixture with hydrogen chloride from the production of chloroformates. For this purpose, the phosgene/hydrogen chloride gas mixture leaving the condenser mounted on the reaction vessel is firstly brought into contact with cold solvent, with the phosgene being preferentially absorbed in the solvent. The absorbed phosgene together with the partially also absorbed hydrogen chloride is then continuously separated off again from the solvent in a distillation column. For this purpose, the feed is introduced between stripping section and enrichment section and a runback to the distillation column, which completely frees the gas mixture taken off at the top of solvent, is produced by means of an overhead condenser. The phosgene is completely liquefied and separated off from the gas stream obtained and is fed to a storage container. A disadvantage of the process disclosed is the high demand for cooling power at a low temperature level.

An alternative method of fractionating gaseous mixtures composed of hydrogen chloride and phosgene is described in DE 102 600 84. The document discloses a process in which the phosgene is condensed under superatmospheric pressure and the condensed phase is stripped to remove the hydrogen chloride in a subsequent process step. The stripping is necessary since appreciable amounts of hydrogen chloride dissolve in the condensate because of the superatmospheric pressure and, according to the teaching of the document, these have a disadvantageous effect in phosgenation reactions. A disadvantage of the process disclosed is that, owing to the prevailing condensation pressure, a further process step for separating off the dissolved hydrogen chloride is necessary. The document gives no information on the recovery of gaseous phosgene. The document states that the hydrogen chloride/phosgene separation can be carried out under a high pressure, but this increases the safety risks. In addition, the generation of high pressure is energy-consuming. As an alternative, a description is given of a separation at very low temperatures, but this is likewise energy-consuming and in addition leads to high contents of hydrogen chloride in the liquid, phosgene-containing phase.

U.S. Pat. No. 3,544,611 describes a process for preparing organic isocyanates. The liquid reaction solution is fed into the middle part of a distillation column in order to take off hydrogen chloride at the top and phosgene and isocyanate at the bottom. The bottom stream is fed to a further distillation column in order to separate the isocyanate and phosgene from one another and recirculate phosgene to the reaction. A disadvantage of the process described is the high pressure of 10-50 bar at which the distillation has to be operated in order to be able to separate the mixtures by distillation at economically advantageous coolant temperatures.

The abovementioned documents do not disclose specific instructions relating to technical procedures allowing excess phosgene to be recovered in a very economical way and recirculated to the phosgenation reaction. As a result, the processes lose economical attractiveness.

WO 2007/014 936 discloses a process for preparing diisocyanates by reaction of diamines with a stoichiometric excess of phosgene in the gas phase, with the excess phosgene being at least partly recirculated to the reaction and the phosgene stream to the reactor containing less than 15% by weight of hydrogen chloride before mixing with the amine. According to the teaching of this document, this is said to improve the time of operation of the reactors since precipitation of amine hydrochlorides is said to be reduced. A disadvantage of such high contents of inert hydrogen chloride gas in the phosgene gas is that it leads, as a result of increased recycle streams, to an increase in operating costs and also to large apparatuses and thus high plant construction costs. In an embodiment described, the excess phosgene and the hydrogen chloride formed are firstly separated off from the essentially gaseous reaction mixture and the excess phosgene is then at least partly recirculated to the reaction, with hydrogen chloride being separated off from this recirculated phosgene in such a way that the phosgene stream contains less than 15% by weight of hydrogen chloride before mixing with the amine stream. No information is given regarding the content of solvent in the recirculated phosgene stream. The document teaches that the separation is preferably carried out by means of a combination of a distillation and a scrub. Here, the phosgene is scrubbed out of the hydrogen chloride-containing stream by means of a scrubbing medium. The separation of the phosgene and the hydrogen chloride from this loaded scrubbing medium is preferably carried out by distillation. The scrub and the distillation can, according to the description, be operated at pressures of from 1 to 10 bar absolute. Further details regarding the separation of phosgene from the loaded scrubbing medium are not disclosed by the document.

According to the teaching of WO 2008/086 922, the phosgene must not contain more than 1000 ppm by weight of chlorine before mixing with the amine in a gas-phase phosgenation reaction since otherwise the risk of materials embrittlement would arise because of the high temperatures. According to this teaching, a certain amount of chlorine is always formed because of the dissociation of phosgene at high temperatures, so that removal of this chlorine is necessary. In addition, the document discloses an embodiment in which the gas mixture containing phosgene, hydrogen chloride and chlorine is firstly subjected to a partial condensation (page 18, line 30) and scrub (page 19, line 18). Here, a liquid phase containing phosgene, scrubbing medium, hydrogen chloride and chlorine is obtained. This is then freed of the low boilers chlorine and hydrogen chloride in a first rectification (referred to as c)). In a subsequent step, phosgene and scrubbing medium are separated from one another in a second rectification (referred to as e)) (page 20, line 26 to page 21 line 11). The document discloses two embodiments of the second rectification column: in the first, the rectification column has only a stripping section so that the overhead product is taken off without purification via separation-active internals at the top. The characterization of the composition of the bottom product is not clear; it is recirculated to the phosgenation reaction. Nothing is said about the further use of the low boiler stream eL.

In the preferred second embodiment, the second rectification additionally has an enrichment section which, at an appropriate reflux ratio, makes it possible for the overhead stream to consist essentially of pure phosgene which can be used without further purification in the phosgenation. In this embodiment having an enrichment section, the bottom stream consists essentially of pure scrubbing liquid.

WO 2009/037 179 discloses a process for preparing isocyanates in the gas phase, in which the freshly produced phosgene is introduced without prior condensation into the gas-phase reaction. As a result of the apparatus and energy for phosgene condensation, intermediate storage of liquid phosgene and phosgene vaporization being able to be dispensed with, the phosgene holdup in the plant is reduced and the energy for vaporizing the phosgene is saved (page 5, lines 32-42). A disadvantage of this process is the lack of opportunity of separating off accompanying components present in the fresh phosgene, which otherwise contaminate the hydrogen chloride stream discharged from the process.

Furthermore, this document describes the method of separating phosgene from a gas mixture with hydrogen chloride and recirculating the phosgene which has been separated off to the gas-phase phosgenation by means of a combined scrub and multistage distillation.

On the subject, the document states that a scrubbing liquid loaded with phosgene and hydrogen chloride is firstly obtained in a first step by scrubbing of the phosgene/hydrogen chloride gas mixture with a scrubbing liquid. This is followed by a first distillation step in which the hydrogen chloride is very largely removed from the phosgene-containing scrubbing solution and is returned to the preceding scrubbing step, followed by a second distillation step in which the previously obtained scrubbing solution is separated into gaseous phosgene and very largely phosgene-free scrubbing liquid. The gaseous phosgene is introduced into the gas-phase phosgenation, while the scrubbing liquid is reused for scrubbing of the phosgene/hydrogen chloride gas mixture. The document does not disclose how the phosgene-scrubbing liquid separation is configured in terms of apparatus or the purity of the recirculated phosgene stream which can be achieved.

According to the general teaching of this document, a two-stage distillation process is consequently the process of choice in order to recover gaseous phosgene from a phosgene-laden scrubbing medium for recirculation to the phosgenation reaction. The omission of the condensation and storage of fresh phosgene is the only specific measure named by the document for achieving a lower phosgene holdup. Although a process consisting of two distillation steps (and thus the use of separation apparatuses having a significant phosgene holdup) are proposed as preferred embodiment, no details regarding the configuration in terms of apparatus of the two distillation steps are given, in particular not in respect of a configuration in terms of apparatus which minimizes the phosgene holdup.

WO 2011/003 532 discloses a process for preparing isocyanates by reaction of primary amines with phosgene in a stoichiometric excess in the gas phase, in which the excess phosgene is subsequently recovered and recirculated to the reaction. The recovery of phosgene from the gas mixture containing phosgene and hydrogen chloride is carried out in two stages. In the first step (hydrogen chloride-phosgene separation), the gas mixture containing hydrogen chloride and phosgene which leaves the reactor is separated into a gaseous stream containing mainly hydrogen chloride and a liquid stream containing phosgene and the liquid stream previously obtained is converted in a second step (phosgene gas production) into a gaseous, phosgene-containing stream, wherein the pressure in the first process step is lower than the pressure in the second process step. The process is advantageous since it allows the recovery of phosgene from the liquid, phosgene-containing scrubbing medium solution in only one step (phosgene gas production). In a preferred embodiment, phosgene gas production is carried out in a distillation column having 2-45 theoretical plates. The column can contain a stripping section and/or enrichment section; the column preferably contains both a stripping section and an enrichment section, with the feed stream preferably being introduced between stripping section and enrichment section. The column is preferably operated at a temperature at the bottom of 140-220° C.

In a preferred embodiment, the column is provided with an overhead condenser. The overhead condenser is preferably operated at a coolant entry temperature of from −25 to 0° C. The condensate produced by means of the overhead condenser can be partly or entirely recirculated to and/or taken off from the column; the condensate is preferably recirculated in its entirety to the column.

Disadvantages of the preferred embodiment are the large dimensions of the column for phosgene gas production and also the expensive use of cold for producing a runback stream.

In an alternative embodiment, phosgene gas production is carried out by the phosgene-containing liquid stream from the hydrogen chloride-phosgene separation being separated by partial vaporization into a gaseous stream containing phosgene and possibly inerts and a liquid stream. For this purpose, the liquid stream obtained from the hydrogen chloride-phosgene separation is fed into an evaporator whose temperature at the bottom is preferably 100-220° C. Compared to the abovementioned preferred embodiment, this embodiment reduces the apparatus and refrigeration energy costs and also the liquid phosgene holdup, but allows only low purities of the gaseous phosgene stream produced and of the stream which contains predominantly scrubbing medium and is discharged in liquid form from the bottom of the evaporator.

In addition, the document teaches that, in order to optimize the energy consumption, the phosgene-containing liquid stream from the hydrogen chloride-phosgene separation is preferably conveyed indirectly to phosgene gas production, i.e. is fed to phosgene gas production after particularly preferably heating to 5-175° C. by heat exchange with other process streams.

According to example 5 in WO 2011/003 532, phosgene gas production is configured in the form of a stripping column, i.e. without enrichment section. (In distillation technology, the term enrichment section refers to the part made separation-active by means of internals above the inlet of a distillation column. The enrichment section increases the purity of the overhead product. In a stripping column, the stream to be distilled is introduced at the top of the distillation column, so that a stripping column does not have an enrichment section.) The phosgene solution obtained from the hydrogen chloride-phosgene separation is pumped directly, i.e. without prevaporization, at a temperature below 10° C. to the top of the stripping column. Gaseous phosgene containing about 0.2% by weight of solvent is taken off at the top of the stripping column. However, this embodiment has the disadvantage that, owing to the low temperature at the top of the desorption column, no energy-saving heat integration by preheating and partial prevaporization can be achieved. Furthermore, the phosgene solution can have different compositions and temperature because of varied process parameters (including phosgene excess in the reaction, reactor outlet temperature, amount of solvent for the quench, amount of solvent for phosgene absorption) and because of process fluctuations. When introduction occurs directly via the top of the stripping column, this inevitably leads to an altered and possibly fluctuating composition and temperature of the phosgene return stream to the reaction, since a regulable overhead condenser which has a stabilizing effect is not available in this embodiment. Fluctuating conditions of the phosgene return stream can lead to a lower energy efficiency, reduced reaction yield, increased operating costs and reduced availability.

WO 2011/003 532 mentions the possibility of hydrogen chloride-phosgene gas mixtures from a plurality of reaction lines being treated in a single hydrogen chloride-phosgene separation. However, it is not disclosed how the sufficiently stable column pressure which is essential for parallel operation of a plurality of reactors can be ensured even in the case of quick operating point changes. Since gas-phase reactors have a narrow favorable load range, a quick operating point change is advantageous, for example, on starting up and running down individual reactors.

A series of procedures by means of which mixtures of hydrogen chloride and phosgene and also possibly solvent can be fractionated in order to allow recirculation of the phosgene into the reaction are thus known from the prior art. However, the prior art does not go into detail regarding the problems of making phosgene recirculation controllable by means of regulation even under relatively difficult conditions. Such relatively difficult conditions can be, for example, unexpected process fluctuations, for example triggered by fluctuations or brief interruptions in individual parts of the plant, e.g. in fresh phosgene production. However, planned alterations to the process can also become challenges in terms of regulation. This is, in particular, the case when a gas-phase phosgenation is to be carried out in a plurality of reactors connected in parallel, the gaseous reaction products of which are worked up in a joint work-up section.

The parallel operation of a plurality of manufacturing apparatuses having the same configuration is nothing unusual in the industrial production of chemical products. The division of a desired total production capacity over a plurality of manufacturing apparatuses (production lines or trains) operated in parallel is advisable when, inter alia, The construction of the apparatuses allows a smaller maximum production capacity than the desired total capacity of the production plant (cf. "Rules of Thumb for Chemical Engineers", 4th Ed., 2005, page 242, chapter "*Process Evaluation—What Size should a plant be?*")

Partial processes or apparatuses have to be shut down occasionally for cleaning purposes, e.g. because of a tendency to suffer from fouling, without total production being shut down for this purpose (Ullmann's Encyclopedia of Industrial Chemistry, Wiley-VCH, Weinheim, 2012, chapter "*Chemical Plant Design and Construction*", volume 8, page 267)

Partial processes or apparatuses have a higher risk of going down than is acceptable for the total plant (Ullmann's Encyclopedia of Industrial Chemistry, Wiley-VCH, Weinheim, 2012, chapter "*Chemical Plant Design and Construction*", volume 8, page 273)

Partial processes or apparatuses have a more restricted possible load range than is to be made possible for the total plant.

EP-A-570 799 states that gas-phase reactors for the phosgenation of amines have only a narrow favorable load range and that solids formation can occur in the reactors, making interruptions to production for cleaning purposes necessary. For these reasons, inter alia, the installation of a plurality of reaction lines for phosgenation which can be operated in parallel can be advantageous. To reduce the apparatus costs, it can, on the other hand, be advantageous nevertheless to configure upstream and/or downstream process steps (e.g. phosgene production, amine vaporization, hydrogen chloride-phosgene separation) jointly for all reaction lines.

EP-A-2 196 455 describes, inter alia, an embodiment of a production process for isocyanates in which the crude product is fed to two reaction lines having a joint reaction termination zone (quench).

If a joint phosgene gas production is operated so as to feed the recovered phosgene stream in gaseous form to a plurality of reaction lines, phosgene gas production and the reactors are connected to one another via a gas space, so that a change in the process pressure in one apparatus acts on the connected apparatuses. This applies particularly when there are no actively regulable pressure-increasing or pressure-reducing elements in the connection between phosgene gas production and reactors. Sudden changes, in particular, in process parameters (e.g. safety shutdown or load change in a reaction line) lead to undesirable instabilities in the total plant, possibly through to the need to take the total plant out of operation. An important parameter for trouble-free and stable operation of the reaction is ensuring of a constant phosgene excess in the phosgenation reaction. In order to ensure a constant stream of gaseous phosgene, a constant supply of pressure of the phosgene gas source, i.e., for example, a distillation column, is essential. The regulation of the pressure in this distillation column is therefore of substantial importance for the total process stability.

In order to lower the apparatus costs and, taking into account the increasing desire for safety, to minimize the phosgene holdup, it would be advantageous to be able to dispense with the enrichment section and possibly also the overhead condenser of the distillation column used for phosgene gas production. However, the omission of the overhead condenser makes pressure regulation more difficult. In addition, the prior art does not disclose any process which would combine the omission of the enrichment section with an energy-efficient preheating/prevaporization of the feed to phosgene gas production.

The prior art does mention that an inert material, e.g. solvent, can be introduced into the gas-phase reaction, with the range of the possible solvent contents described in the phosgene return stream extending up to 10 mass 90. However, in all specific working examples disclosed which describe the recovery and recirculation of phosgene used in excess back into the gas-phase reaction, a very low solvent content in the phosgene stream is nevertheless obviously sought in practice (see, for example, the document WO 2011/003 532 discussed comprehensively above: according to this, only a few ppm of solvent are permitted in order to minimize the energy usage; in example 5, mention is made of a solvent concentration of 0.2%, which is the maximum value disclosed in a specific working example). This is achieved by either the phosgene-solvent separation column being equipped with an enrichment section and being operated with runback or by a low temperature level being maintained at the top of the column (in WO 2011/003 532, a temperature of the feed to the top of the column of not more than 10° C. is mentioned).

The prior art accordingly does not give any information as to how the advantages of
 a. phosgene gas production without enrichment section (lower apparatus costs, lower phosgene holdup, lower condensation energy costs) and
 b. energy-efficient heat integration for feed preheating and/or vaporization can be combined with one another.

There was therefore a need for a process which is very simple in terms of apparatus and favorable in terms of energy for preparing isocyanates, which keeps the phosgene holdup very low without thereby making the recirculation of the excess phosgene to the reaction more difficult, in particular under conditions which are challenging in terms of regulation (e.g. the use of a plurality of reaction lines operated in parallel with joint work-up).

SUMMARY

Bearing in mind this need, the present invention provides a continuous process for preparing an isocyanate by phosgenation of the corresponding primary amine, which comprises the steps:

(i) reaction of the primary amine with an excess of phosgene in the gas phase;
(ii) treatment of the process product obtained in (i) with a solvent at a temperature which is below the boiling point of the isocyanate and above the decomposition temperature of the corresponding carbamoyl chloride to give a gaseous stream (ii-1) containing hydrogen chloride and unreacted phosgene and a liquid stream (ii-2) containing solvent and isocyanate;
(iii) separation of the hydrogen chloride and phosgene present in the stream (ii-1) to give a liquid phosgene-containing stream (iii-1) and a gaseous stream (iii-2) containing hydrogen chloride;
(iv) partial vaporization of the liquid phosgene-containing stream (iii-1) to give a two-phase process product;
(v) introduction of the two-phase process product from step (iv) at the top of a distillation column, from which a gaseous phosgene-containing stream is taken off at the top;
(vi) recirculation of the gaseous phosgene-containing stream from step (v) to step (i) (recirculation of "recycle phosgene");
(vii) work-up of the liquid stream (ii-2) containing solvent and isocyanate obtained in step (ii) to isolate the desired isocyanate.

The procedure according to the invention, namely to arrange the inflow to the distillation column from step (v) at the top of this column, i.e. omit an enrichment section, leads to increased solvent contents in the gaseous phosgene-containing overhead product of this column compared to the embodiment with enrichment section customary in the prior art. However, it has surprisingly been found that the increase in the volume flow which is inevitably associated therewith (and is not desirable per se) takes a back seat behind the many other advantages of the process of the invention (simplification in terms of apparatus, lower phosgene holdup, operational stability, improved opportunity for energy integration) and the advantages significantly predominate overall.

Furthermore, the procedure according to the invention, namely to vaporize the liquid phosgene-containing stream (iii-1) only partially in step (iv) and feed a two-phase process product into the distillation column in step (v), makes it possible to use the prevaporizer used in step (iv) as regulating device, as a result of which the hitherto customary overhead condenser of this distillation column, which in the prior art also performs regulating tasks, can be dispensed with in principle and is preferably also not used in the process of the invention. The mode of operation of the prevaporizer enables the solvent content in the gaseous phosgene-containing overhead product to be set in a targeted manner (e.g. to 5.0% by mass at a temperature of the two-phase process product on introduction into the distillation column of 100° C.), as explained in more detail below. (All compositions indicated in this text relate the mass of the respective component based on the mass of the respective total stream, unless another definition is given in the corresponding passages.)

The inventive combination of configuration in terms of apparatus (no enrichment section in the distillation column of step (v); in a preferred embodiment, omission of the overhead condenser) and mode of operation (only partial vaporization in the prevaporizer of step (iv)) makes it possible to regulate the pressure in the production of gaseous recycle phosgene (i.e. the pressure in the distillation column of step (v)) in a manner which is so stable that only small deviations from the intended value occur even in the event of sudden, considerable operating point changes of the phosgene flow to all reactors used in step (i). This quality of the pressure regulation allows, as will be explained in detail below, a (at least partially) gaseous, phosgene-containing feed stream to the stage of production of gaseous recycle phosgene to be used as manipulated variable of the pressure regulation in a preferred embodiment.

DETAILED DESCRIPTION

Various embodiments of the invention are described in more detail below. Here, all embodiments can be combined with one another in any way, unless the contrary is apparent to a person skilled in the art from the context.

Step (i) of the invention, the actual gas-phase phosgenation, can in principle be carried out by a process described in the prior art, as described, for example, in EP-A-570 799 and WO-A-2007/014936.

Here, it is possible to use either aliphatic or aromatic monoamines and polyamines. Preference is given to using aromatic amines, particularly preferably aromatic diamines, which can be brought into the gas phase without appreciable decomposition.

Examples of preferred aromatic amines are toluenediamine (TDA), in particular 2,4-TDA and 2,6-TDA and mixtures thereof, diaminobenzene, naphthalenediamine (NDA) and 2,2'-, 2,4'- or 4,4'-methylenedi(phenylamine) (MDA) or isomer mixtures thereof. Particular preference is given to toluenediamine (TDA), especially 2,4-TDA and 2,6-TDA and mixtures thereof.

Furthermore, amines, in particular diamines, based on aliphatic or cycloaliphatic hydrocarbons having from 2 to 18 carbon atoms are particularly suitable. Particularly well-suited amines are 1,6-diaminohexane, 1-amino-3,3,5-trimethyl-5-aminomethylcyclohexane (IPDA) and 4,4'-diaminodicyclohexylamine.

The starting amines are generally vaporized and heated to from 200° C. to 600° C., preferably from 200° C. to 500° C., particularly preferably from 250° C. to 450° C., and optionally diluted with an inert gas such as $N_2$, He, Ar or with vapors of an inert solvent, e.g. aromatic hydrocarbons, optionally with halogen substitution, e.g. chlorobenzene or o-dichlorobenzene, before introduction into the reaction space before carrying out the process of the invention.

The vaporization of the starting amines can be carried out in all known vaporization apparatuses, with preference being given to vaporization systems in which a small working content is conveyed at a high circulation rate through a falling film evaporator; to minimize the thermal stress on the starting amines, the vaporization operation can, as indicated above, optionally be assisted by introduction of inert gas and/or vapors of an inert solvent. As an alternative, the vaporization can also be carried out in specific vaporization apparatuses having very short residence times, as are described, for example, in EP-A-1 754 698.

In the process of the invention, phosgene is used in an excess over the amine groups to be reacted. A molar ratio of phosgene to amine groups of from 1.1 to 20, preferably from 1.2 to 5, is preferably present. The phosgene, too, is heated to temperatures of from 200° C. to 600° C. and optionally diluted with an inert gas such as $N_2$, He, Ar or with vapors of an inert solvent, e.g. aromatic hydrocarbons without or with halogen substitution, e.g. chlorobenzene or o-dichlorobenzene, before being fed into the reaction space.

The process of the invention in step (i) is preferably carried out in such a way that the separately heated reactants are introduced via at least one mixing device into at least one reaction space, mixed and reacted under preferably adiabatic reaction conditions, ensuring suitable reaction times. The isocyanate is subsequently condensed by cooling of the gas stream, with cooling being carried out to a temperature above the decomposition temperature of the corresponding carbamoyl chloride, i.e., for example, toluenediamine acid chloride in the case of TDA.

The residence time necessary for reaction of the amine groups with the phosgene to form isocyanate is in the range from 0.05 to 15 seconds, depending on the type of amine used, the initial temperature, the adiabatic temperature increase in the reaction space, the molar ratio of amine used and phosgene, any dilution of the reactants with inert gases and also the reaction pressure selected.

In step (i), particular preference is given to using reactors having essentially rotationally symmetric reaction spaces, in which the gaseous starting materials, optionally diluted with inerts, are fed into the at least one mixing space according to the jet mixer principle (Chemie-Ing. Techn. 44 (1972) page 1055, FIG. 10).

Preference is given to neither the reaction space nor any mixing apparatuses or mixing spaces having heating surfaces which could give rise to thermal stressing with the consequence of subsequent reactions such as isocyanurate or carbodiimide formation or cooling surfaces which can give rise to condensation with the consequence of deposits. The components are thus, disregarding any radiation and conduction losses, preferably reacted adiabatically, with the adiabatic temperature increase in mixing apparatus and reactor or reactor alone being established by means of the temperatures, compositions and relative amounts of the feed streams and also the residence time in the mixing apparatuses and the reactors. A nonadiabatic reaction of the components is also possible in the process of the invention.

After the phosgenation reaction has occurred in the reaction space, the gaseous reaction mixture, which comprises the isocyanate formed, phosgene and hydrogen chloride, is freed of the isocyanate formed and any reactions still proceeding are stopped by treatment with a solvent in step (ii) ("quench").

This can, for example, be carried out by the process product which continuously leaves the reaction space being subjected, after leaving the reaction space, to a condensation in an inert solvent, as has been recommended for other gas-phase phosgenations (cf. EP-A-0 749 958).

However, the condensation is preferably carried out by the process product leaving the reaction space being conveyed into a reaction termination zone into which one or more suitable solvent streams ("quenching liquids") are sprayed. Rapid cooling of the gas mixtures without the use of cold surfaces can be carried out thereby, as described in EP-A-1 403 248.

In any case, the treatment with solvent is carried out at a temperature which is below the boiling point of the isocyanate and above the decomposition temperature of the corresponding carbamoyl chloride, so as to give a gaseous stream (ii-1) containing hydrogen chloride and unreacted phosgene and a liquid stream (ii-2) containing solvent and isocyanate. To isolate the isocyanate selectively from the gaseous reaction mixture, solvent such as chlorobenzene and/or dichlorobenzene maintained at a temperature of from 80° C. to 200° C., preferably from 80° C. to 180° C., or isocyanate or mixtures of the isocyanate with chlorobenzene and/or dichlorobenzene kept in these temperature ranges are particularly well-suited. A person skilled in the art can easily predict the proportion by mass of the isocyanate which condenses in the quench or goes through the quench in uncondensed form from the physical data at a given temperature, pressure and composition. Likewise, it is easy to predict the proportion by mass of the excess phosgene, hydrogen chloride and inert gas optionally used as diluent which goes through the quench in uncondensed form or dissolves in the quenching liquid.

The gas mixture (ii-1) leaving the condensation or quenching stage is preferably freed of residual isocyanate by means of a suitable scrubbing liquid in a downstream gas scrub. The preparation of the pure isocyanate is preferably carried out subsequently by distillative work-up of the stream (ii-2), optionally after the latter has been combined with further isocyanate from the gas scrub.

In step (iii), the hydrogen chloride and phosgene present in the stream (ii-1) are separated to give a liquid phosgene-containing stream (iii-1) and a gaseous stream (iii-2) containing hydrogen chloride.

The gas mixture entering the fractionation in step (iii) generally contains from 1 to 50% by mass of HCl, preferably from 3 to 40% by mass of HCl, particularly preferably from 5 to 35% by mass of HCl and very particularly preferably from 7.5 to 30% by mass of HCl, based on the mass of the gas mixture. This gas mixture generally contains from 5 to 90% by mass of phosgene, preferably from 15 to 85% by mass of phosgene, particularly preferably from 25 to 80% by mass of phosgene and very particularly preferably from 40 to 75% by mass of phosgene, based on the mass of the gas mixture. The content of solvent in the gas mixture is generally from 0.01 to 60% by mass, preferably from 0.05 to 40% by mass and particularly preferably from 0.1 to 10% by mass, based on the mass of the gas mixture. The solvent can be present in vapor form or as liquid. The gas mixture can additionally contain inert gases in a total amount of generally from 0 to 10% by mass, preferably from 0.0001 to 8% by mass and particularly preferably from 0.001 to 5% by mass, based on the mass of the gas mixture. The gas mixture can generally contain from 0 to 10% by mass, preferably from 0.001 to 7.5% by mass and particularly preferably from 0.05 to 5% by mass, of reaction product, based on the mass of the gas mixture.

The separation according to the invention in step (iii) can be carried out according to various embodiments, as are, for example, comprehensively described in WO 2011/003532 (page 11, line 31 to page 19 line 11) and can also be used in the process of the invention. Thus, an absorption in a solvent is suitable as is a partial condensation with a subsequent scrub or a complete or partial condensation with a subsequent distillation or stripping step.

A particularly preferred embodiment of this process step is an absorption in a solvent. Particular preference is given to carrying out the absorption in the solvent which is also used for the quench (step (ii)).

In a particularly preferred embodiment, the absorption is carried out in a sequence of at least two absorption steps, optionally in combination with partial condensation steps, with at least one absorption step being carried out isothermally and at least one absorption step being carried out adiabatically. Very particular preference is given to the first absorption step being carried out isothermally, and the following absorption step being carried out adiabatically. In a particularly preferred embodiment, the same solvent which was used in step (ii) is in each case used for the adiabatic absorption step and for the isothermal absorption step. Preference is also given to the gas leaving the last absorption step being freed of any remaining traces of phosgene and solvent by condensation by cooling by means of a heat exchanger. In a preferred embodiment, the isothermal absorption and subsequent adiabatic absorption are carried out in a single apparatus (=a single absorption column), with the cooling of the gas stream leaving the absorption particularly preferably also being carried out in the same apparatus. This has the advantage that the number of flanges is reduced thereby, contributing to an increase in safety when handling phosgene. It has the further advantage of energy saving since energy losses in the connecting pipes are minimized by the compact construction in one apparatus.

In a further embodiment, step (iii) is carried out by partial condensation with a subsequent scrub. In this particular embodiment, the gas mixture is firstly partially condensed. The remaining gas stream is introduced from the bottom into an absorption column and scrubbed in countercurrent with the solvent. The heat of absorption is removed by means of external heat exchangers. For this purpose, the liquid can be taken off in its entirety or in part, preferably in its entirety, preferably at various places on the absorption column, and cooled by means of an external cooler.

A further possible embodiment for carrying out step (iii) is the partial or complete condensation of phosgene, subsequently a distillation or stripping step in a column in order to remove the dissolved HCl from the bottom product phosgene and subsequently a scrub of the overhead product HCl obtained in the first step using a solvent for absorption of the phosgene remaining in the gas stream after the condensation. The liquid stream obtained at the bottom of the distillation or stripping step has only a small loading with dissolved HCl and/or inert gases and can be introduced into step (iv).

The above-described process alternatives for carrying out the step (iii) all give a gaseous stream (iii-2) and a liquid stream (iii-1). The HCl-containing gas stream (iii-2) has a sufficient purity and can generally be processed further without further purification.

In one embodiment of the present invention, the fresh phosgene which has to be introduced in order to replace the phosgene consumed in step (i) is added in step (iii) and thus becomes a constituent of the liquid phosgene-containing stream (iii-1) obtained in this step. There are various possibilities for this. Thus, fresh phosgene can, for example, in the embodiment of step (iii) in which this step comprises absorption in a solvent, be introduced, optionally after liquefaction, into the bottom of the corresponding absorption column.

The gas stream (iii-2) leaving the step (iii) contains essentially HCl and possibly traces of phosgene. Apart from HCl, the stream can additionally contain inert gases and/or solvent and also traces of reaction by-products. The stream contains from 80 to 100% by mass, preferably from 90 to 100% by mass and particularly preferably from 95 to 100% by mass, of HCl, based on the mass of the gas stream (iii-2). This gas stream contains not more than 0.8% by mass of phosgene, preferably not more than 0.4% by mass and particularly preferably not more than 0.2% by mass of phosgene, based on the mass of the gas stream (iii-2). To achieve optimization in terms of energy, it can be preferable to permit at least 1 ppm by mass of phosgene, preferably at least 5 ppm by mass of phosgene, based on the mass of the gas stream (iii-2), with the abovementioned maximum limits for the phosgene content applying in both cases. The gas stream (iii-2) leaving step (iii) is generally under a pressure of from 1.00 to 4.00 bar absolute, preferably from 1.01 to 3.00 bar absolute and particularly preferably from 1.02 to 2.00 bar absolute, at the outlet from the process step. The gas stream obtained from step (iii) generally has a temperature of from −40 to 30° C., preferably from −20 to 20° C. and particularly preferably from −15 to 10° C., at the outlet from the process step. For the purposes of the present invention, the outlet from the process step is the gas exit port of the last apparatus belonging to this process step.

Regardless of the precise configuration of step (iii), the liquid phosgene-containing stream (iii-1) leaving this step contains phosgene together with solvent (solvent which has not been completely separated off in step (ii) and optionally the absorption solvent from step (iii)). Dissolved HCl and/or dissolved inert materials and also possibly dissolved reaction by-products may also still be present. The stream (iii-1) contains from 30 to 90% by mass, preferably from 35 to 85% by mass and particularly preferably from 40 to 70% by mass, of phosgene, based on the mass of the liquid phosgene-containing stream (iii-1). In addition, this stream contains from 10 to 70% by mass, preferably from 15 to 65% by mass and in particular preferably from 30 to 60% by mass, of solvent, based on the mass of the liquid phosgene-containing stream (iii-1). Furthermore, this liquid stream (iii-1) can contain from 0 to 5% by mass, preferably from 0.1 to 3.5% by mass and particularly preferably from 0.5 to 2.5% by mass, of dissolved hydrogen chloride, based on the weight of the liquid phosgene-containing stream (iii-1).

The liquid phosgene-containing stream (iii-1) exiting from step (iii) generally has a temperature of from −40 to 20° C., preferably from −25 to 15° C. and particularly preferably from −20 to 10° C. This stream is generally under a pressure of from 1.00 to 4.00 bar absolute, preferably from 1.01 to 3.00 bar absolute and particularly preferably from 1.02 to 2.00 bar absolute, at the outlet from the process step. For the purposes of the present invention, the outlet from the process step for the liquid phosgene-containing stream is the liquid exit port from the apparatus(es) belonging to this process step. The pressure measured there is caused by the hydrostatic pressure of the liquid column in the apparatus (es).

This stream (iii-1) is then partially vaporized in step (iv). This partial vaporization of the stream (iii-1) can, for example, be effected by:
  use of a regulated prevaporizer (i.e. introduction of heat at approximately the pressure of the distillation column of step (v), formation of a vapor phase as a result),
  regulated flash evaporation (partial vaporization by lowering of the pressure) or
  regulated superheating of the liquid feed stream (iii-1) under superatmospheric pressure (i.e. heating the liquid feed under superatmospheric pressure to a temperature which is above the boiling point of the mixture at the pressure of the distillation column in step (v)).

The preheating and partial vaporization reduces the energy costs by the introduction of heat at the bottom of the distillation column in step (v) to a high temperature level being partly replaced by introduction of heat at a lower temperature level in the feed to the column.

The preheating and partial vaporization can optionally also be carried out in a plurality of steps (i.e. by means of a plurality of apparatuses and/or a plurality of heating media).

The preheating and partial vaporization can, particularly because of the low to moderate temperature level, optionally also be carried out by heat integration with suitable process streams and/or waste heat streams (condensate, low-pressure steam) and thus allows particularly energy-efficient operation of the plant, in contrast to the prior art independently of the configuration of the distillation column of step (v) with or without enrichment section.

If the preheating and partial vaporization is carried out in a plurality of steps, it is not necessary for all steps to be regulated in respect of heat transfer, which frequently assists heat integration by little reverse effect on other process steps and thereby leads to more robust operational behavior of the overall process.

When preheating and partial vaporization is carried out in a plurality of steps and optionally by means of various heating media, it is also possible for a plurality of these steps to be integrated in one apparatus. Reduced apparatus volumes and further connections between apparatuses and pipes are advantageous from the safety point of view, especially in the case of phosgene-conveying apparatuses, and lead to lower apparatus costs.

The above-described inventive procedure in step (iv) makes it possible to regulate the pressure in the distillation column of the subsequent step (v) (the step of production of gaseous recycle phosgene which in step (vi) is recirculated to the reaction of step (i)) by variation of the amount of the vapor introduced directly into the mixture to be separated in this distillation column. For the purposes of the present invention, the "pressure in the distillation column of step (v)" is the pressure measured at the top of the column. The expression "vapor introduced directly into the mixture to be separated in this distillation column" refers here to streams which contain phosgene vapor and come into contact in terms of material with the mixture to be separated in the distillation column, i.e. refers, in particular, to the vapor fraction obtained in step (iv) (however, it is also possible, as explained in more detail below, for phosgene vapor fractions from another source to be present). In the following, the expression "vapor introduced directly" will also be used for short. A distinction is made between this and heating steam which is introduced via an indirect heating device and is not in contact in terms of material with the mixture to be separated in the distillation column.

Conventional pressure regulating systems for columns use, in the case of overhead product being taken off in vapor form (see Kister: "Distillation Operation" chapter 17.2), either (a) the amount of overhead product taken off itself or (b) the condensation power as manipulated variable, more rarely (c) systems which "breathe" opposite the atmosphere or inert gas or (d) regulation concepts working via the bottom vaporizer. Disadvantages of this procedure of the prior art for the present application would be: (a) the overhead product offtake stream cannot simultaneously be controlled variable and manipulated variable; (b) the use of the condensation power as manipulated variable is not quick enough, in particular in order to make available quickly increasing amounts of phosgene as overhead product stream; the variant (c) is not advantageous because of the phosgene loss and the necessity of introducing inert gas; (d) the use of the bottom vaporizer as manipulated variable is not quick enough (see (b)).

However, it has surprisingly been found that, for the present application, a stable column pressure in step (v) can be regulated particularly well by using an (at least partially) gaseous, phosgene-containing feed stream (the two-phase process product from step (iv)) for producing the gaseous recycle phosgene as manipulated variable of the pressure regulation.

In the present application, the parameters column pressure and amount of phosgene taken off at the top of the distillation column of step (v) are coupled closely to one another, so that the pressure regulation according to the invention, which influences both parameters in parallel, is particularly effective.

In the simplest case, the vapor introduced directly into the distillation column of step (v) consists exclusively of the vapor fraction of the two-phase process product from step (iv). In this embodiment, the fresh phosgene, provided separately, to be introduced to replace the phosgene consumed in step (i) can, if this has not already been introduced in step (iii) and is thus already part of the phosgene present in the two-phase process product from step (iv), be mixed with the gaseous phosgene-containing stream from step (v) (i.e. the "recycle phosgene") before this stream is fed to the reaction of step (i). However, it is also conceivable for the recycle phosgene and the fresh phosgene to be fed separately from one another to the reaction of step (i). In both variants mentioned, fresh phosgene can be fed in unliquefied form, including any inert gases present and any excess carbon monoxide present, from its production directly to the reactor, provided that the desired type of further use of the hydrogen chloride formed in the process permits this in respect of its purity. Otherwise, the fresh phosgene can, likewise in both variants mentioned, preferably be introduced in liquefied form, be vaporized in a separate vaporizer and then be fed to the reaction of step (i).

It is likewise conceivable for fresh phosgene to be introduced in liquid form, for example as a solution in a solvent, preferably as a solution in the solvent used in step (ii), or preferably in pure form, into the distillation column of step (v), e.g. into the bottom of this column, with the bottom of the column then performing the function of a phosgene vaporizer. However, in a preferred embodiment, liquid fresh phosgene is introduced directly at the top of this column, so that the liquid fresh phosgene can partly replace the function of the runback. If, although possible in principle, an overhead condenser of the distillation column of step (v) is not to be omitted, fresh phosgene can also be fed to this overhead condenser in liquid form as runback to the distillation column.

In a preferred embodiment of the process of the invention, variation of the amount of the vapor fed to the distillation column of step (v) is carried out by variation of the proportion of vapor in the two-phase process product produced in step (iv). This is preferably effected by varying the temperature of the two-phase process product from step (iv): the higher this temperature, the greater is the proportion of vapor and vice versa. The temperature of the two-phase process product can, in the case of steam heating, be set by, for example, suitable regulation of the heating steam.

In another embodiment of the process of the invention, the distillation column of step (v) is supplied with gaseous fresh phosgene in addition to the two-phase process product from step (iv), i.e. the vapor introduced directly into the distillation column comprises the vapor fraction of the two-phase process product from step (iv) and fresh phosgene vapor provided separately. It is not necessary to use a fully gaseous phosgene stream for this purpose; rather, it is also possible to introduce a further two-phase stream (i.e. a stream containing liquid and gaseous fractions) into the distillation column of step (v). In this embodiment, too, variation of the amount of the vapor fed to the distillation column of step (v) can be carried out by variation of the proportion of vapor in the two-phase process product produced in step (iv). However, it can also be carried out by variation of the proportion of vapor in the further stream containing phosgene vapor (if the stream is not already entirely present in vapor form but instead has a variable proportion of liquid). A combination of the two measures is also conceivable.

In this embodiment in particular (but not restricted to this embodiment), it can be advantageous to carry out the variation of the amount of the vapor introduced directly into the distillation column of step (v) by variation of the total amount (i.e. the sum of liquid fraction and gaseous fraction) of two-phase process product from step (iv) fed to this column and/or by variation of the total amount of separately provided, optionally two-phase, stream containing phosgene vapor which is fed to this column. Here, the proportion of vapor, expressed as proportion by mass of the total stream from step (iv), in the two-phase process product produced in step (iv) is preferably kept essentially constant. "Essentially constant" here means that a proportion of vapor which has been set fluctuates by not more than an absolute value corresponding to 3% of the intended value of the proportion of vapor. If the variation of the total amount of an above-described additionally introduced, optionally two-phase, stream containing phosgene vapor is additionally or exclusively used for the regulating task, the proportion of vapor in this is preferably kept essentially constant. "Essentially constant" here means that a proportion of vapor which has been set fluctuates by not more than an absolute value corresponding to 3% of the intended value for the proportion of vapor.

This embodiment allows the gaseous fresh phosgene also to be used as pressure-regulating feed stream.

The regulation of the pressure by means of the gaseous feed to the distillation column of step (v) enables the overhead condenser as regulating device and the enrichment section to be dispensed with. A relatively high proportion of solvent in the recycle phosgene, compared to that disclosed in specific working examples in the prior art, is intentionally accepted and has not been found to be disadvantageous in practice (in respect of reaction yield, by-products, etc.). The proportion of solvent in the recycle phosgene can be set in a targeted manner by means of the feed temperature to the distillation column of step (v). Tracking of the feed temperature enables the proportion of solvent in the recycle phosgene to be kept constant even in the case of altered feed parameters (composition, pressure), which represents an advantage over the prior art (for example an unregulated stripping column). A higher feed temperature leads, inter alia, to an increased proportion of solvent in the recycle phosgene, but on the other hand also reduces the energy costs by a higher heat integration contribution and waste heat utilization for feed heating and by a reduced energy consumption for heating the recycle phosgene stream. A feed temperature (i.e. the temperature of the two-phase process product from step (iv) on introduction into the distillation column of step (v)) of from 50° C. to 150° C., preferably from 80° C. to 120° C., particularly preferably from 90° C. to 110° C., and a proportion of solvent in the gaseous phosgene-containing stream from step (v) of from 1.0% by mass to 15% by mass, preferably from 2.5% by mass to 10% by mass, particularly preferably from 3.0% by mass to 7.5% by mass, at a pressure in the distillation column of step (v) of from 10 mbar above to 1500 mbar above ambient pressure (measured at the top of the column) have been found to be particularly advantageous.

In step (vi) according to the invention, the gaseous phosgene-containing stream obtained in step (v) is recirculated, optionally after addition of fresh phosgene (see above) into the reaction of step (i).

The work-up of the liquid stream (ii-2) containing solvent and isocyanate which is obtained in step (ii) in order to recover the desired isocyanate can be carried out in step (vi) by any method of the prior art. The work-up is preferably carried out by distillation. This step is adequately known from the prior art and is preferably carried out as described in EP 1 371 635 B1, especially in paragraphs [0014] to [0018].

The omission of the enrichment section and preferably also the overhead condenser significantly reduces the liquid holdup with high phosgene proportion in the distillation column of step (v). Based on the overall plant, the phosgene holdup is thereby significantly reduced, i.e. reduced by about 10% to 20%.

The omission of the overhead condenser in the preferred embodiments reduces the apparatus costs, the plant complexity and at the same time the operating costs for condensation energy.

The omission of the enrichment section reduces the volume of the distillation column of step (v) by up to 80%, which leads to significantly lower apparatus costs.

Further advantages of the process of the invention are:
  Dispensing with the enrichment section additionally leads to a significantly reduced pressure drop in the distillation column of step (v). At the same pressure at the top, the pressure at the bottom and the corresponding vaporizer temperature decrease, so that the vaporizer can be made with a smaller area.
  The "intermediate boiler bulge" (e.g. tetrachloromethane) in the distillation column of step (v) is significantly reduced, since more intermediate boilers are discharged at the top and barely accumulate. A breakthrough of the intermediate boiler bulge in an upward or downward direction in the column leads to boiling temperature fluctuations since, inter alia, the bottom temperature is sensitive to changes in the proportion of intermediate boilers. A lower accumulation of intermediate boilers therefore makes regulation easier, in particular regulation of the bottom product to attain freedom from phosgene, since the boiling point of a mixture can be utilized for calculating and regulating the purity of a stream (e.g. the bottom stream) only when the mixture is an essentially pure two-component mixture having widely separated boiling points (e.g. solvent and phosgene). If it is ensured that only the two-component mixture solvent/phosgene is always present in the bottom of the column, the column can in practice be operated reliably enough for it to be used as apparatus for solvent dephosgenation and for dedicated additional apparatuses for this task to be dispensed with.

The mixture taken off as liquid bottom product in step (v), which consists essentially of solvent, is preferably recirculated into the process. This process stream usually has a temperature which is close to the boiling point and therefore has a high temperature level which is not necessary or even undesirable for the process step into which it is recirculated (e.g. the quench). This bottom product stream is therefore particularly suitable for internal heat recovery in the process with cooling of this bottom product stream, e.g. for vaporization of fresh phosgene which is present in liquid form, for heating the gaseous phosgene stream fed into the reaction, for vaporizing or superheating the amine before entry into the gas-phase reactor, for superheating the hydrogen chloride stream to be discharged from step (iii), for preheating or partial vaporization in step (iv), for heating bottom vaporizers in the work-up sequence for the liquid quench product or at another point in this process.

The advantage according to the invention of the opportunity of regulating the pressure in the distillation column of step (v) in a simple and efficient manner, in particular the opportunity of keeping this pressure essentially constant in a simple manner even in the case of changes in the boundary conditions, is particularly apparent when the production of the desired isocyanate is carried out in a plurality of (generally in n, where n is a natural number ≥2) reaction lines connected in parallel, in each case comprising the steps (i) and (ii), which have in common a small number (i.e. a maximum of n−1) work-up lines in which the steps (iii) to (v) are carried out.

Particular preference is given to combining the process streams $(ii-1)_1$ to $(ii-1)_n$ obtained in the n reaction lines and working them up together in a single work-up line. In this embodiment, the gaseous phosgene-containing stream obtained in the single work-up line is preferably divided into n individual streams in step (vi) and these are preferably distributed over the n reaction lines.

However, it is also possible to distribute the reaction products (ii-1) from, for example, three reaction lines over two work-up lines. This can, for example, be effected by firstly combining the individual streams $(ii-1)_1$ to $(ii-1)_3$ and then dividing the resulting stream into two streams. In this embodiment, the gaseous phosgene-containing streams obtained in each case in the not more than (n−1) work-up lines (in the selected example in two work-up lines) are preferably divided over all n reaction lines (in the selected example thus over three reaction lines). This can be effected by firstly combining the individual streams and then distributing the resulting stream over the n reaction lines.

The invention claimed is:

1. A continuous process for preparing an isocyanate by gas phase phosgenation of the corresponding primary amine, comprising:
  (i) reacting the primary amine with an excess of phosgene to obtain a process product;
  (ii) treating the process product with a solvent at a temperature which is below the boiling point of the isocyanate and above the decomposition temperature of the corresponding carbamoyl chloride to give a gaseous stream (ii-1) containing hydrogen chloride and unreacted phosgene and a liquid stream (ii-2) containing solvent and isocyanate;
  (iii) separating the hydrogen chloride and phosgene present in the stream (ii-1) to give a liquid phosgene-containing stream (iii-1) and a gaseous stream (iii-2) containing hydrogen chloride;
  (iv) partially vaporizing the liquid phosgene-containing stream (iii-1) to give a two-phase process product;
  (v) introducing the two-phase process product at the top of a distillation column, from which a gaseous phosgene-containing stream is taken off at the top;
  (vi) recirculating the gaseous phosgene-containing stream to step (i); and
  (vii) working up the liquid stream (ii-2) containing solvent and isocyanate to isolate the isocyanate.

2. The process of claim 1, wherein step (iii) comprises absorption of phosgene in a solvent which is fed together with phosgene in the liquid stream (iii-1) into step (iv).

3. The process of claim 1, comprising regulating the pressure in the distillation column by varying the amount of the vapor introduced directly into the mixture to be separated in the distillation column.

4. The process of claim 3, wherein the vapor introduced directly into the mixture to be separated in the distillation column comprises:
  a) the vapor fraction of the two-phase process product, and
  b) phosgene vapor from a further, optionally two-phase, stream introduced into the distillation column.

5. The process of claim 4, wherein varying the amount of the vapor introduced into the mixture to be separated in the distillation column comprises:
   a) varying the total amount of the two-phase process product introduced into the distillation column, or
   b) varying the total amount of the further, optionally two-phase, stream containing phosgene vapor which is introduced into the distillation column or
   c) by both a) and b).

6. The process of claim 5, wherein the proportion of vapor
   a) in the two-phase process product or
   b) in the further, optionally two-phase, stream containing phosgene vapor or
   c) in both streams a) and b)
   is kept essentially constant.

7. The process of claim 4, wherein the varying of the amount of the vapor introduced into the mixture to be separated in the distillation column comprises:
   a) varying the proportion of vapor in the two-phase process product which is introduced into the distillation column, or
   b) varying the proportion of vapor in the further stream containing phosgene vapor which is introduced in the distillation column, said further stream containing phosgene vapor being two-phase, or
   c) by both a) and b).

8. The process of claim 3, wherein the vapor introduced directly into the mixture to be separated in the distillation column of step (v) consists entirely of the vapor fraction of the two-phase process product produced in step (iv).

9. The process of claim 8, wherein the varying of the amount of the vapor introduced into the mixture to be separated in the distillation column comprises varying the total amount of the two-phase process product which is introduced into the distillation column.

10. The process of claim 9, wherein the proportion of vapor in the two-phase process product produced in step (iv) is kept essentially constant.

11. The process of claim 8, wherein the varying of the amount of the vapor introduced directly into the mixture to be separated in the distillation column comprises varying the proportion of vapor in the two-phase process product.

12. The process of claim 1, wherein the distillation column does not have an overhead condenser.

13. The process of claim 1, comprising carrying out steps (i) and (ii) in n reaction lines in parallel, where n is a natural number $\geq 2$, and process streams $(ii\text{-}1)_1$ to $(ii\text{-}1)_n$ obtained in the n reaction lines are worked up in not more than $(n-1)$ work-up lines in which steps (iii) to (v) are carried out.

14. The process of claim 13, wherein the process streams $(ii\text{-}1)_1$ to $(ii\text{-}1)_n$ obtained in the n reaction lines are combined and worked up together in a single work-up line.

15. The process of claim 13, wherein the gaseous phosgene-containing streams obtained in each of the not more than $(n-1)$ work-up lines are distributed over all n reaction lines.

16. The process of claim 14, wherein the gaseous phosgene-containing stream obtained in the single work-up line is divided into n individual streams and distributed over the n reaction lines.

* * * * *